United States Patent [19]

Salomaa et al.

[11] Patent Number: 4,478,094
[45] Date of Patent: Oct. 23, 1984

[54] LIQUID SAMPLE HANDLING SYSTEM

[75] Inventors: Kari Salomaa, Jenner; Roy Merrill, Orinda; Richard Leath, El Cerrito; Timothy Wennberg; Joseph Widunas, both of San Francisco, all of Calif.

[73] Assignee: Cetus Corporation, Emeryville, Calif.

[21] Appl. No.: 489,866

[22] Filed: May 5, 1983

Related U.S. Application Data

[63] Continuation-in-part of Ser. No. 459,973, Jan. 21, 1983, abandoned.

[51] Int. Cl.³ ............................................. G01N 35/06
[52] U.S. Cl. ............................... 73/863.32; 73/864.14; 422/65; 422/100
[58] Field of Search ........................ 73/863.32, 864.14; 422/65, 100

[56] References Cited

U.S. PATENT DOCUMENTS

| | | |
|---|---|---|
| 3,188,181 | 6/1965 | Peterson et al. |
| 3,327,535 | 6/1967 | Sequeira . |
| 3,443,439 | 5/1969 | Cruz . |
| 3,581,575 | 6/1971 | Butler . |
| 3,696,971 | 10/1972 | Maclin . |
| 3,776,700 | 12/1973 | Gallant . |
| 3,802,782 | 4/1974 | Natelson . |
| 3,982,438 | 9/1976 | Byrd . |
| 3,991,617 | 11/1976 | d'Autry ............................ 73/864.14 |
| 4,047,438 | 9/1977 | Sekine . |
| 4,158,035 | 6/1979 | Haase et al. . |
| 4,215,092 | 7/1980 | Souvaniemi ...................... 73/864.14 |

Primary Examiner—S. Clement Swisher
Attorney, Agent, or Firm—Albert P. Halluin; Ralph L. Freeland, Jr.; Thomas E. Ciotti

[57] ABSTRACT

An automatic liquid transfer system includes a horizontally translatable table and a vertically translatable set of pipettes. The table accommodates a titer tray having a multiplicity of receptacles to be filled, or holding liquid samples to be diluted, and a rack housing plural rows of disposable tips. During each cycle in a serial dilution process, a fresh set of tips are picked up by the pipettes and used to transfer liquid in a sterile manner from a sample or diluent source to a row of wells in the titer tray, or from one row to a succeeding row of wells where it is mixed with diluent. Thereafter, the tips are discharged back into the rack to maintain sterile conditions during the process. A sensor is provided on the machine to detect whether all of the tips in each set are disengaged and another set successfully picked up.

25 Claims, 14 Drawing Figures

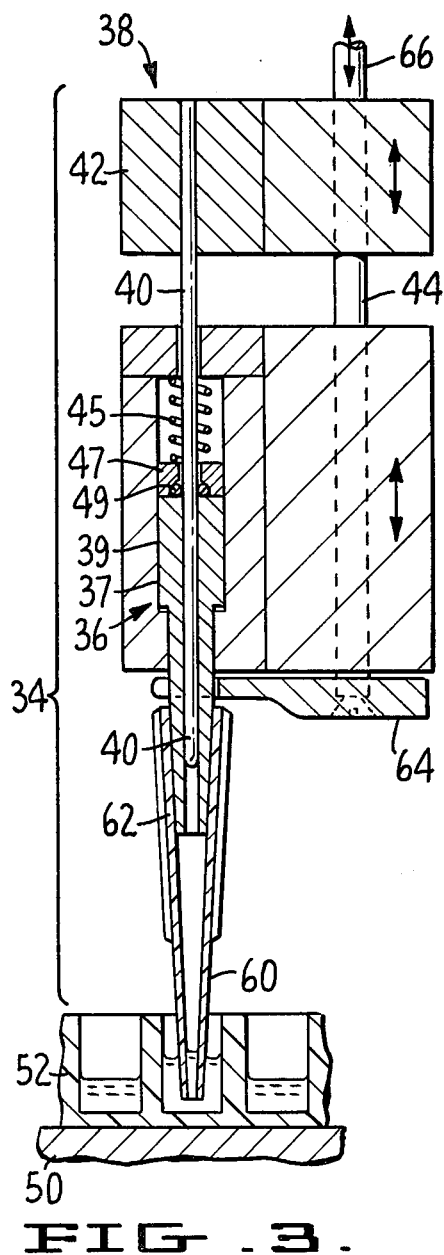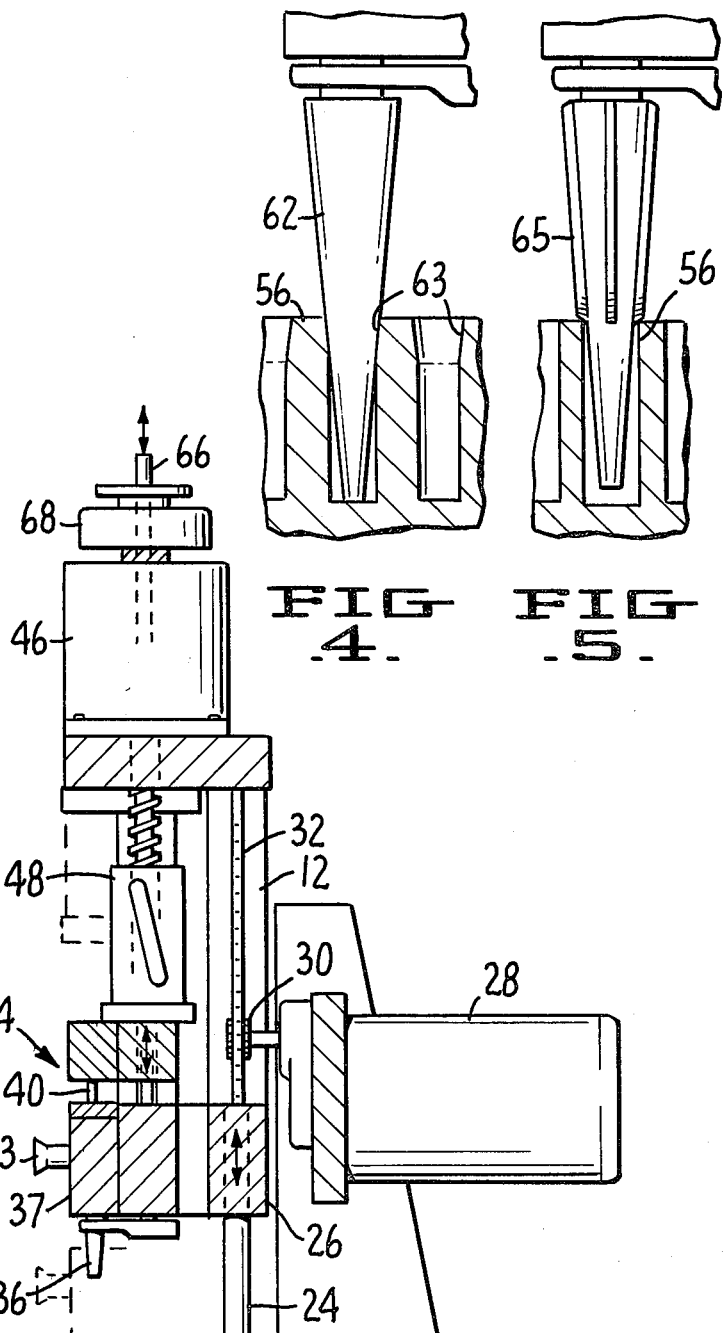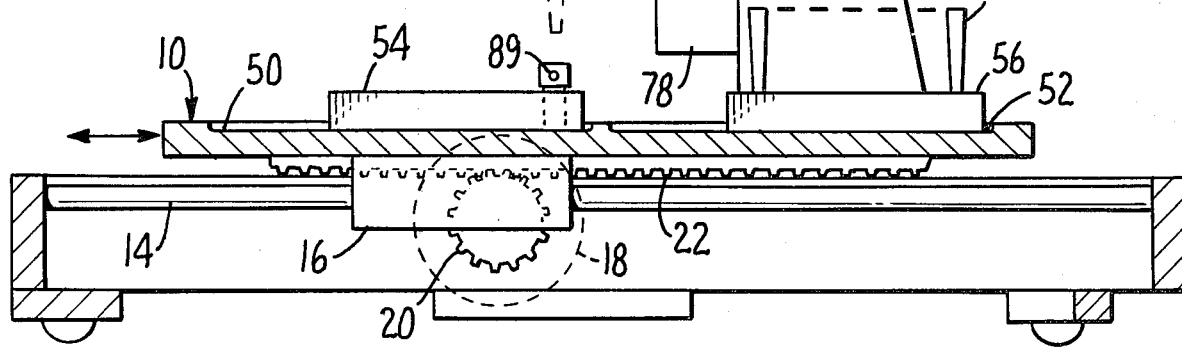

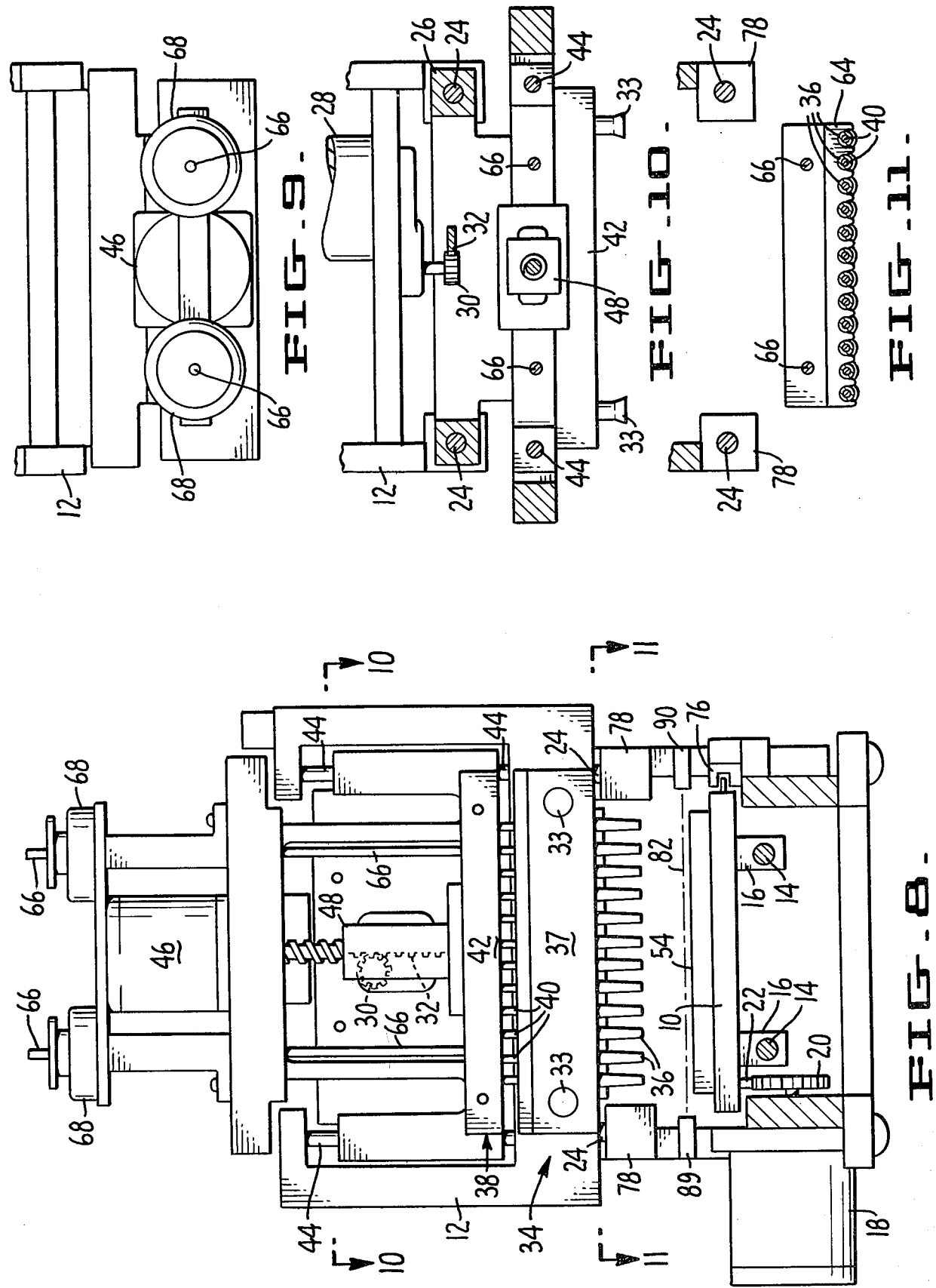

LIQUID SAMPLE HANDLING SYSTEM

CROSS-REFERENCE TO RELATED APPLICATION

This application is a continuation-in-part of copending application U.S. Ser. No. 459,973, filed Jan. 21, 1983 now abandoned.

BACKGROUND OF THE INVENTION

The present invention is directed to a method for performing automatic transfer of liquid samples between a plurality of receptacles. More specifically, it is directed to a system for filling, or transferring liquid samples between, a multiplicity of separate liquid receptacles, such as is required in initial filling and serial dilution of liquid samples in microtiter trays where each receptacle holds only about one tenth to ten milliliters of liquid. Such a serial dilution system basically involves mixing the sample with successively increasing proportions of a diluent in separate receptacles thereby to obtain a series of successively decreasing concentrations of the sample. The various sample concentrations can then be assayed to determine a particular property. For example, the sample might be a serum and the assay might be used to determine which concentration of the serum provides optimum results when reacted with a particular substance.

Initially, serial dilution of a sample was performed manually, wherein different proportions of the sample would be mixed with diluent contained in different respective test tubes, for example with the aid of a syringe or pipette. This procedure consumed a considerable amount of time when a number of different concentrations were required. Consequently, machines for automatically or semi-automatically performing serial dilutions were developed. One example of such a machine is disclosed in U.S. Pat. No. 3,188,181. The serial dilution machine disclosed in that patent includes a horizontally movable carriage that accommodates a rack of test tubes. A vertically movable syringe holder housing a plurality of off-the-shelf syringes respectively connected to pipettes is raised and lowered by means of a cam to bring the pipettes into the liquid volume in a row of test tubes within the rack. A cam operated pumping head oscillates the syringes to mix fluid in the pipettes with that in the test tubes. After mixing, fluid is withdrawn from the test tubes, the syringe holder is lifted, and the carriage is incremented to another row of test tubes to repeat the operation. When the serial dilution operation is complete, a first row of test tubes in the rack might contain undiluted concentrations of the sample, the second row of test tubes would contain a 50/50 concentration of the sample, the third row would be a 25/75 concentration, and so forth, depending on the amount of liquid transferred by the pipettes.

It is an object of the present invention to provide a novel system for automatically effecting transfer of liquid between receptacles without cross contamination or errors in the quantity of liquid so transferred and which is particularly useful in performing serial dilution of small liquid samples with substantially improved performance over that possible with the machine of the previously noted patent. More particularly, when handling certain types of solutions, it is desirable to prevent cross-contamination between various sample concentrations. Typically, this is done in the manual method by utilizing disposable tips on the pipettes that withdraw the liquid from one receptacle and mix it with diluent in another. After each mixing operation, the tip is removed from the pipette and replaced with a clean one. However, heretofore known serial dilution machines do not offer the ability to change tips between each cycle in the serial dilution process. Consequently, when prevention of cross-contamination is desired, the machine must effect a multi-step washing process for the pipettes, or provide a flushing process between each cycle in the process. The washing process substantially increases the time that is required to effect a serial dilution since a number of steps are added in each cycle of the process. The flushing procedure generates a considerable amount of waste liquid that must be disposed of.

Accordingly, it is a more particular object of the present invention to provide a novel automatic serial diluter arrangement that is capable of automatically changing disposable tips on pipettes in a quick and efficient manner in any desired cycle of the serial dilution process from initial fill of the liquid receptacles through any of a selectable plurality of addition or subtraction steps to transfer liquid between the receptacles.

SUMMARY OF THE INVENTION

These objects are achieved in accordance with the present invention by providing at least two work stations on a table that translates horizontally beneath pipettes that withdraw and inject liquid samples. In a preferred form, at least one work station accommodates a titer tray or similar such structure having plural rows of receptacles for housing the liquid sample and the diluents, and at least a second work station accommodates a rack that houses plural rows of disposable pipette tips. The pipettes themselves have tapered ends that can be inserted into and frictionally engage the tips when a head assembly on which they are mounted is moved downwardly to bring them together. Once the tips are picked up, the table is translated to bring a selected row of wells in the titer tray underneath the tips, and the head is then lowered to insert the tips within the wells. Some of the sample in the wells is aspirated into the pipettes through actuation of plungers in each pipette and, after raising the head, the table is incremented one or more steps to bring another, generally the next successive, row of wells into registry with the tips. The head is then lowered to insert the tips into the diluent in these wells and the plunger oscillated to mix the sample with the diluent. The head is then raised so that the pipette tip is just above the meniscus of liquid in the well after all the liquid is expelled from the tip. The plunger is then extended to expel all of the liquid with the aid of some excess air from the pipettes and surface tension on any liquid between the tip and the well. The table is then translated to bring the rack housing the tips beneath the pipettes, and a solenoid controlled tip ejector means is actuated to push the tips from the tapered ends of the pipettes and back into the rack. Alternatively, the tips may be ejected through a slot in the table (or at another station on the table) into a trough or collector container. The table then can be incremented one step to bring a fresh set of tips into registry with the pipettes, and the cycle repeated. In a preferred form the volume of each tip is greater than the liquid volume of the titer tray receptacles so that all fluid is moved in and out of the receptacle without substantial liquid contact with the plunger of the pipette.

In accordance with another feature of the present invention, a detector can be provided to determine when the pipettes fail to pick up all of the tips in a row, to thereby prevent the situation in which a sample in one well is not serially diluted into all the various desired concentrations through failure to draw the sample into a pipette because of a missing tip. Similarly, a detector to determine that all tips have been ejected from their respective pipettes prior to pick up of the next row of tips may be provided.

The movement of all of the various elements of the machine can be monitored and controlled as desired by a computer, to thereby provide continuous monitoring of the process and flexibility in filling and transferring liquids for the serial dilution process.

These and other features of the present invention are discussed in greater detail hereinafter with reference to a preferred embodiment thereof illustrated in the accompanying drawings.

BRIEF DESCRIPTION OF THE DRAWINGS

FIG. 2 is a sectional side view of the serial dilution machine taken in the direction of arrows 2—2 in FIG. 1;

FIG. 3 is an enlarged, sectional side view of one embodiment of a pipette tip in a tip support tray well;

FIG. 4 is an enlarged, sectional side view of a preferred form of pipette tip supported in a tip tray well;

FIG. 5 is an enlarged, sectional side view of the plunger and pipette assembly;

FIG. 8 is a sectional front view of the automatic serial dilution machine taken in the direction of arrows 8—8 in FIG. 1;

FIG. 9 is a partial top plan view of the machine;

FIG. 10 is a sectional top view taken along the section line 10—10 of FIG. 8;

FIG. 11 is a sectional top view taken along the section line 11—11 of FIG. 8.

DETAILED DESCRIPTION

Figure 1:
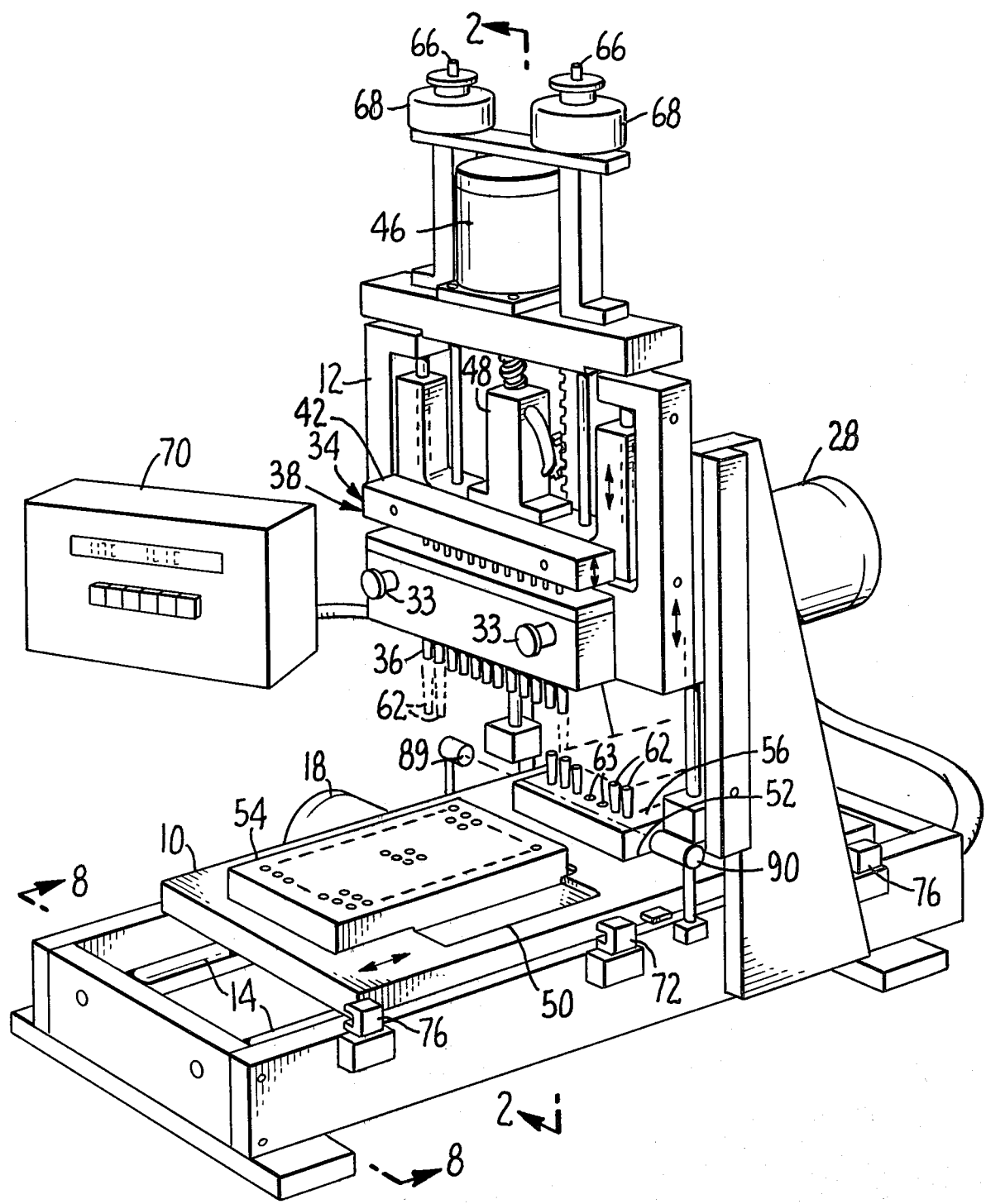
FIG. 1 is a perspective view of a serial dilution machine implementing the features of the present invention.

Referring to FIGS. 1 and 2, an automatic serial dilution machine suitable for carrying out the method of the present invention includes two main movable parts, a horizontally translatable table 10 and a vertically translatable head assembly 12. As best illustrated in FIG. 2, the table 10 is mounted for horizontal translation on hardened guide rods 14 by means of slide bearings 16. Translation of the table is provided by a stepper motor 18 through a pinion 20 connected to the motor and a rack 22 mounted on the underside of the table. Similarly, the head 12 is mounted for vertical translation on guide rods 24 by means of slide bearings 26. Translation of the head assembly is provided by a stepper motor 28 through a pinion 30 and a rack 32.

The head assembly 12 supports a pipette and plunger assembly 34. This assembly includes a series of pipettes 36 that are arranged in a row transverse to the axis of translation of the table 10. The pipettes are removably attached to the head assembly by means of a mounting block 37, and connecting pins 33 and move therewith. A plunger mechanism 38 is mounted on the head assembly for vertical movement relative to the pipettes. The plunger mechanism includes a series of plunger rods 40, one being disposed respectively within each pipette 36. All of the rods are mounted on a common actuator bar 42 for concurrent vertical movement. The bar 42 is translated along guide rods 44 by means of a stepper motor 46 and a lead screw drive mechanism 48. As best illustrated in the detailed sectional diagram of FIG. 3, translation of the plunger rods 40 relative to the pipettes 36 changes the internal volumes of the pipettes, causing fluid to be aspirated into or expelled from them. An air tight seal is provided between each rod and the top of its associated pipette by means of an O-ring 49, held by grommet 47 and compliance spring 45. Each pipette 36 includes a piston section 39 which is reciprocably mounted in a cylinder 35 formed in mounting block 37. Pipette 36 is thereby restrained vertically by spring 45 so that during the tip loading step, pipette 36 can slide vertically in block 37 against compliance spring 45. This allows all pipettes to reliably pick up tips of slightly different dimensions and to assure that the open ends of tips 62 are at the same elevation relative to table 10 and titer tray 54.

Figure 6:
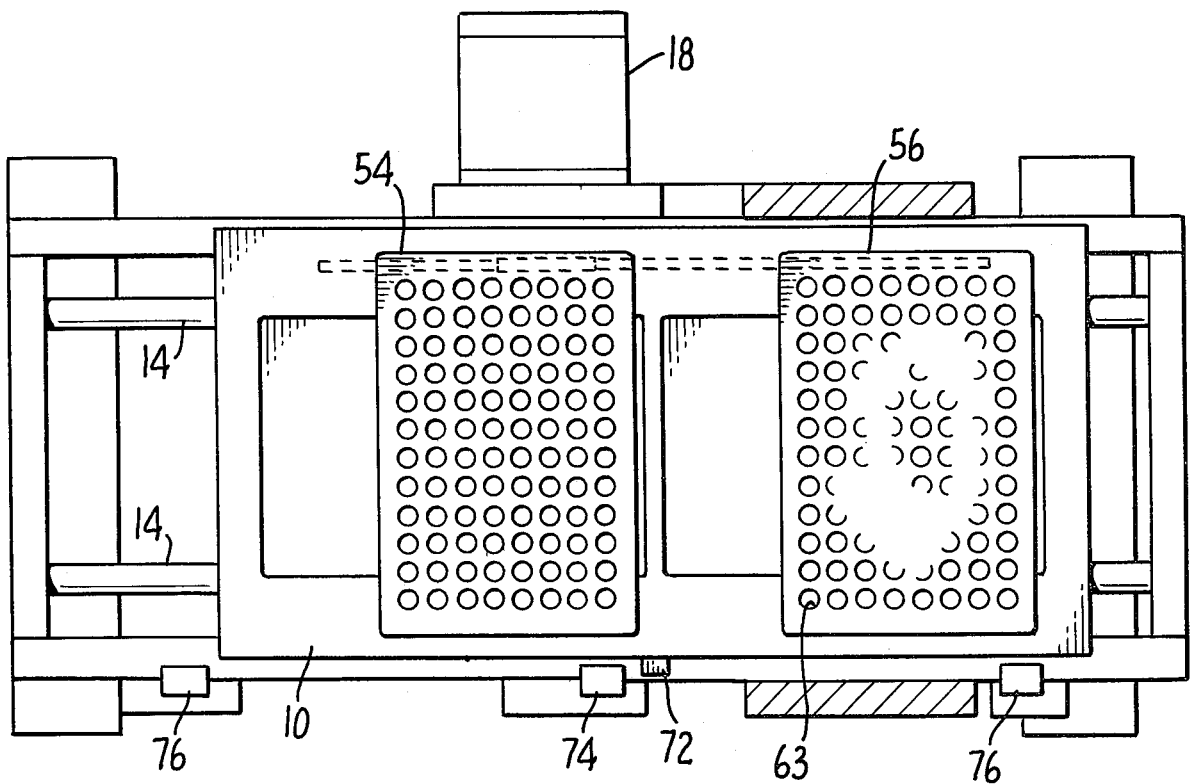
FIG. 6 is a top view of the table showing the trays arranged thereon for a 12×7 diluter configuration.
Figure 7:
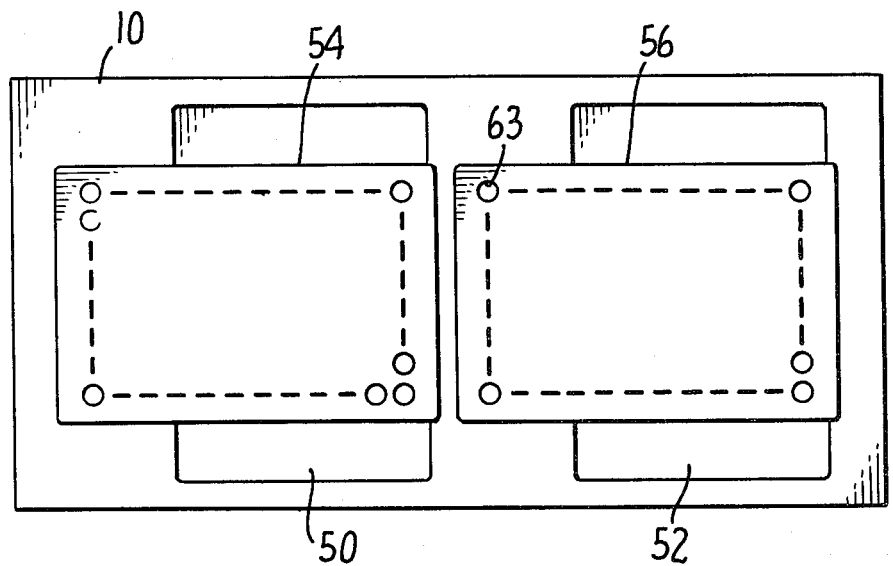
FIG. 7 is a top view of the table showing the trays arranged for an 8×11 diluter configuration.

The table 10 includes two work stations 50 and 52 for respectively accommodating two trays. One of the trays can be a conventional titer tray 54 that includes a matrix arrangement of wells for housing the liquid sample and the diluent. The other tray 56 at the rear work station 52 can be a tip tray that contains a similar arrangement of receptacles that accommodate disposable pipette tips. A typical titer tray contains 96 wells in a 12×8 matrix pattern. As illustrated in FIG. 6, the tray 54 can be accommodated at the forward work station 50 in a transverse orientation to perform a 12×7 serial dilution, wherein the first row of wells is filled with a predetermined volume of the sample to be diluted, and the remaining wells are filled with the diluent. In this case, the tip tray 56 is also oriented to present twelve receptacles in a row across the width of the tray. Alternatively, as illustrated in FIG. 7, the trays 54 and 56 can be oriented in the longitudinal direction of the table 10 to effect an 8×11 serial dilution.

Referring again to the detailed side view of FIG. 3, the bottom end 60 of each pipette 36 is tapered on its exterior surface so as to receive and frictionally engage the inner surface of disposable pipette tip 62 constructed in accordance with the present invention. For example, the tip 62 might be made of a non-wettable polypropylene material. The tips 62 in a row of wells or receptacles 63 in the tip tray 56 are inserted onto and engage the respective ends of the pipettes 36 when the head assembly 12 is lowered by the stepper motor 28 after the table 10 has brought one row of tips 62 into registry with the pipettes. As indicated, the volume of each tip 62 is a substantial portion of the total volume of the cylinder formed by the barrel of pipette 36 and the interior volume of the tip. As best seen in FIGS. 4 and 5, support of each tip 62 in receptacle 63 of tray 56 is either by end support as in FIG. 4 or on ends of the bottom flutes 65 formed on the exterior of tips 62. The wall of receptacles 63 are arranged to center tip 62 for engagement with tapered end 60 of pipette 36.

The subsequent removal of the tips 62 from the pipettes is accomplished with a tip ejector means. The tip ejector means includes a comb-like plate 64 that is best illustrated in FIG. 11. The plate has recesses that accommodate the pipettes, and its teeth surround a substantial portion, e.g., 180°, of the exterior circumference of each pipette barrel. The plate 64 is connected to and supported by a pair of vertically translatable rods 66 mounted on the head assembly 12. These rods are translated by means of a pair of solenoids 68 mounted on the top of the head assembly. When the solenoids 68 are deactuated, the ejector plate 64 is maintained in the upper position illustrated in FIG. 5. Actuation of the solenoids moves the plate vertically downward, to push the tips 62 down and release them from their frictional engagement with the ends of the pipettes 36.

The operation of each of the stepper motors 18, 28 and 46, and the solenoids 68 is controlled by a suitable microprocessor 70. Basically, the microprocessor 70 functions as a pulse generator to control the sequence of operations of each of these elements, and thus the interrelated movements of the table 10, the head assembly 12, the plunger assembly 34 and the tip ejector plate 64 to effect serial dilution of a sample in the tray 54 at the forward work station 50. Since the stepper motors provide a predetermined amount of rotation in response to each actuating pulse applied thereto, accurate positioning of the movable elements can be obtained through appropriate control of the number of actuating pulses supplied by the microprocessor.

In addition to controlling these various movable elements, the microprocessor 70 also monitors their movement through appropriately positioned sensors. For example, a sensor arrangement for the table 10 can include a blade 72 that is attached to and extends from the side of the table, and a Hall-effect sensor 74 that detects when the blade 72, and hence the table 10, passes through a predetermined reference point in its translation. Each time the table passes through this point, the Hall-effect sensor 74 sends a signal to the microprocessor 70 that enables the microprocessor to update information relating to the table's position. Thus, if the stepper motor 18 should miss an actuating pulse during translation of the table, or if the pulse count stored within the microprocessor 70 should not coincide with the position of the table, the error will not be carried over to successive cycles of operation.

In addition to the reference sensor 74, a pair of limit sensors 76 can be disposed at the respective ends of the path of travel of the table. A signal sent by these sensors indicates that the table is nearing the end of its travel, and provides an indication to the microprocessor 70 to interrupt the supply of power to the stepper motor 18 or take some other such corrective action. Similar sensor arrangements are provided to monitor the movement of the head assembly 12 and the plunger bar 42.

Furthermore, a sensor can be provided on the machine to detect whether all of the tips in a row of the tray 56 have been picked up by the pipette assembly. Referring to FIG. 8, this sensor can include an electrical-optical mechanism comprising an LED 89 or similar such light emitting device on one side of the table and a photoelectric element 90 on the other side of the table. The two elements are aligned with the row of pipettes 36. When one or more tips 62 are present within the row of wells 63 registered with the sensor, the light beam 82 from the LED will be broken and will not reach the photoelectric element 90. However, if all of the tips in a row are successfully picked up by the pipette assembly, the beam will extend across the tray 56 and be detected by the photoelectric element. By proper positioning LED 89 and photoelectric element 90, possible pick up of tray 56 itself, as by friction between tips 62 and wells in tray 56, can also be detected.

Figure 12:
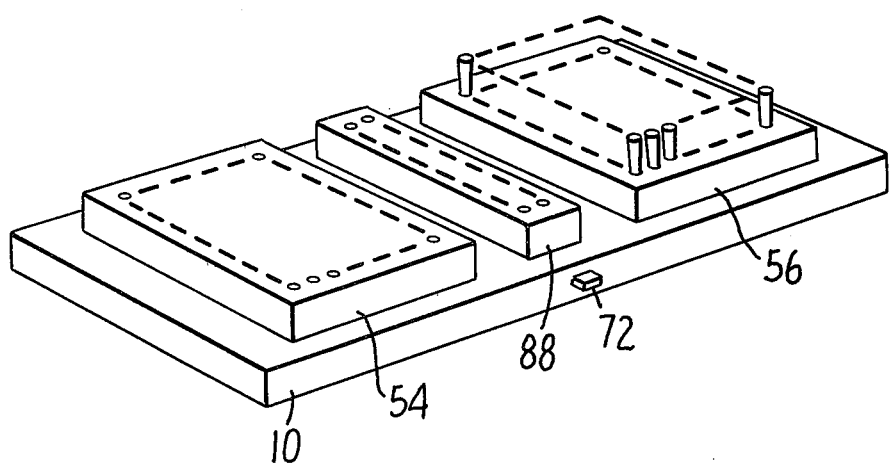
FIG. 12 is a perspective view of an alternate embodiment of a serial dilution machine including a fluid transfer or supply tray between the tip supply tray and the microtiter tray.
Figure 13:
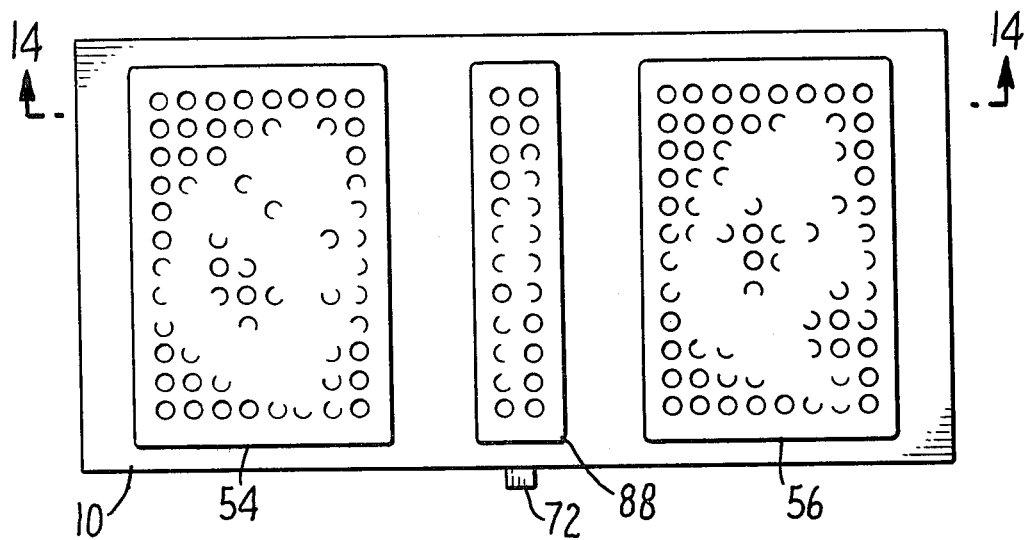
FIG. 13 is top plan view of the FIG. 12 table embodiment.
Figure 14:
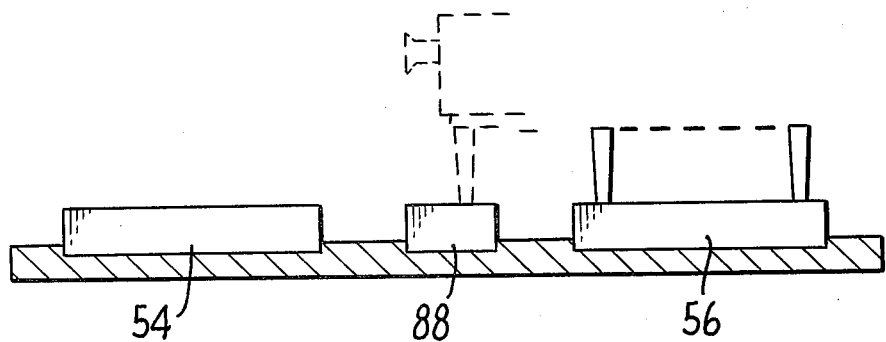
FIG. 14 is a sectional side view taken in the direction of arrows 14—14 in FIG. 13.

FIGS. 12 to 14 illustrate an alternative embodiment of the moveable table arrangement of the present invention. This embodiment includes another microtiter tray 88 between sample tray 54 and tip supply tray 56. Tray 88 may contain either a liquid supply of biological material or a reagent for initially filling the titer tray receptacles. While shown as a plurality of individual wells, tray 88 may be a common supply trough or pan. For example the initial charge of sample material may be injected into a first row of receptacles in tray 54 and after replacement of tips 62 from tray 56, the remaining wells in 56 filled with diluent transferred from another portion of tray 88 or a separate supply of liquid from another tray. As mentioned above, after use, pipette tips may be ejected into empty receptacles in tip tray 56. However, it is also contemplated that another portion of table 10 would permit collection of all used tips. This may either be a slot in table 10 (not shown) permitting drop of the tips into a bin below the table, or a collection bin located at another position on the table.

In operation, the automatic serial dilutor basically functions to pick up a row of tips in the tray 56, insert them in one row of wells in the titer tray 54, extract some of the liquid sample from these wells, inject the tips into the diluent in the next successive row of wells, oscillate the plungers to mix the liquid, position the tips to expel all liquid and then return the tips to the tray 56. This operation is set forth in greater detail with reference to the following example of a program that can be used by the microprocessor to effect a serial dilution process.

| Step | Command | Action |
|------|---------|--------|
| 001 | Table to position M | Bring row M of tray 56 under pipettes |
| 002 | Head assembly down | Load tips |
| 003 | Head assembly up | Pick up tips |
| 004 | Detect for complete tip pick-up | Yes: Go to 005 No: Go to 002 |
| 005 | Table to position N | Bring row N of tray 54 under tips |
| 006 | Head assembly down | Insert tips in wells |
| 007 | Plunger up | Aspirate sample into pipettes |
| 008 | Head assembly up | Remove tips from wells |
| 009 | Table to position N + 1 | Bring next row of tray 54 under tips |
| 010 | Head assembly down | Insert tips in wells |
| 011 | Oscillate plunger | Mix sample and diluent |
| 012 | Head assembly up partially | Tips just out of liquid in wells |
| 013 | Plunger down | Expel sample from pipette |
| 014 | Head assembly up slightly further | Above meniscus |
| 015 | Plunger down beyond initial point | Expel all of sample and some air |
| 016 | Head assembly to top position | |
| 017 | Plunger up to initial point | |
| 018 | Table to position M | Bring empty row of tray 56 under tips |
| 019 | Head down | Insert tips in receptacles |

-continued

| Step | Command | Action |
| --- | --- | --- |
| 020 | Tip ejector down | Release tips |
| 021 | Tip ejector up | |
| 022 | Detect for complete Tip ejection | Yes: Go to 023 No: Go to 020 |
| 023 | Head assembly up | |
| 024 | M = M + 1, N = N + 1 | |
| 025 | Table to position M | |
| 026 | Go to 002 | |

The cycle is repeated a number of times equal to the number of dilutions to be carried out. During any given cycle steps 001–004 and 18–22 can be deleted if changing of the tips is not required.

Prior to the initiation of a serial dilution operation, the microprocessor 70 can be programmed with the volume of liquid that is to be transferred during each cycle of the process. This amount determines the extent to which the plunger rods 40 are raised during step 007 of the program. This action, in turn, determines the concentration of the sample in successive wells of the tray 54. For example, to obtain a dilution spectrum in which the concentration in one row is one-half that of the preceding row, the first row of wells might be filled with 100 $\mu$l of the sample and all other wells filled with 50 $\mu$l of diluent each. The microprocessor would be set up to cause 50 $\mu$l to be transferred from one well to the next succeeding well during each cycle.

During step 011, the plunger rods 40 can be oscillated up and down about 5 times to assure adequate mixing.

At the beginning of each cycle of the serial dilution process, the plunger rods 40 are disposed at a predetermined calibration point within the pipettes. A Hall-effect sensor similar to the type described previously with respect to the table 10 can be used to monitor and control the position of the rods. In step number 014 of the program, after the sample and diluent have been mixed in step 011, the plunger tips are raised so that they are just above the level of liquid in the wells in step 012 and the plunger is returned to the calibration point to expel the liquid from the pipettes in step 013, the tips are raised to a point just above the meniscus of liquid in the receptacle. By then extending the plungers downwardly beyond the calibration point, all liquid is expelled from the pipettes. This action effectively blows the liquid out of the pipettes by causing some air trapped within the pipette to also be ejected and permits any liquid remaining in the tips and extending between the tip and the receptacle to be drawn out of the tip by capillary action due to surface tension acting on the liquid. This step is particularly effective where the tip is made of a non-wettable plastic which as above noted is a preferred material.

Although certain steps have been shown to be discrete, they can be executed simultaneously. For example, steps 016 and 017 might take place at the same time.

It will be appreciated by those of ordinary skill in the art that the present invention can be embodied in other specific forms without departing from the spirit or essential characteristics thereof. The presently disclosed embodiment is therefore considered in all respects to be illustrative and not restrictive. For example, where the term "stepper" motor has been used to describe the preferred embodiment of the motor drive means for table, head assembly and plunger mechanism, it will be apparent that other precise positioning means may be used such as direct current servo motors. The scope of the invention accordingly is indicated by the appended claims rather than the foregoing description, and all changes that come within the range of equivalence thereof are intended to be embraced therein.

What is claimed is:

1. A machine for automatically transferring at least a portion of liquid sample from one or more liquid-containing receptacles to one or more other receptacles, comprising:
   a head assembly translatable between upper and lower positions along a vertical axis;
   means for moving said head assembly along said vertical axis;
   a plunger assembly mounted on said head assembly for movement therewith, said plunger assembly including a row of pipettes having depending ends for receiving tips, a row of plungers respectively disposed within said pipettes, and means for moving said plungers within said pipettes to vary their internal volumes;
   tip ejector means mounted on said head assembly for removing tips disposed on said depending ends of said pipettes;
   a table mounted beneath said head for translation along a horizontal axis, said table having work stations spaced along said axis for respectively accommodating a tray having pipette tip-receiving receptacles and one or more trays providing said liquid-containing receptacles and other receptacles;
   means for moving said table along said horizontal axis to place any selected one of the receptacles in registry with said pipettes; and
   means for controlling each of said moving means for said head assembly, plungers and table and said tip ejector means to effect transfer of liquid between the liquid-containing receptacles and the other receptacles and to replace tips on the ends of said pipettes with other tips disposed in at least some of the pipette tip-receiving receptacles between predetermined liquid transfer steps.

2. The machine of claim 1 wherein said tip ejector means includes a plate disposed adjacent at least a portion of each of said depending ends and movable downward to push disposable tips from said ends.

3. The machine of claim 2 further including at least one solenoid for moving said plate downwardly.

4. The machine of claim 1 wherein said pipette depending ends are tapered to receive and frictionally hold disposable tips disposed in a tray mounted at a work station when said head assembly is moved toward said lower position.

5. The machine of claim 4 wherein said pipette depending ends are vertically reciprocable relative to said head assembly and said plunger assembly includes compliance spring means for restraining movement of said ends relative to said head assembly to permit pick up of tips with slightly different dimensions by said ends.

6. The machine of claim 4 further including means for detecting failure of a tip to be frictionally retained by at least one of said ends when said head assembly moves toward said upper position.

7. The machine of claim 5 wherein said detecting means includes electro-optical means having a line of sight in registry with said row of pipette tips.

8. The machine of claim 1 wherein said head assembly moving means includes a stepper motor and a rackand-pinion arrangement interconnecting said stepper motor and said head assembly.

9. The machine of claim 1 wherein said plunger moving means includes a stepper motor and a lead screw drive mechanism interconnecting said stepper motor and said plungers.

10. The machine of claim 1 wherein said table moving means includes a stepper motor and a rack-and-pinion arrangement interconnecting said stepper motor and said table.

11. The machine of claim 1 wherein said control means includes means for monitoring the position of at least one element including said head assembly, plungers and table.

12. The machine of claim 11 wherein said monitoring means includes a sensor producing a reference signal when a monitored element passes a predetermined point in its path of travel.

13. A method for effecting automatic transfer or dilution of liquid samples between a plurality of liquid receptacles positioned for horizontal movement on a support table and being indexable beneath a vertically movable row of pipettes, comprising the steps of:
(a) charging a predetermined volume of a first liquid into one or more receptacles located at a first work station on said table;
(b) arranging at least a row of pipette tips at a second work station on said table;
(c) moving said table to register said row of pipette tips with the row of pipettes;
(d) lowering said pipettes to engage the tips in said registered row and picking up the engaged tips;
(e) moving said table to register the receptacles of said first work station with said row of pipettes;
(f) inserting the engaged tips in the first liquid in said registered receptacles and withdrawing at least least some of the liquid therefrom into said pipettes;
(g) raising said pipettes;
(h) moving said table to register other receptacles with said pipettes;
(i) lowering said pipettes and expelling the liquid in said pipettes into the other receptacles;
(j) raising said pipettes;
(k) moving the table to bring a selected position at said second work station into alignment with said pipettes;
(l) discharging said engaged tips from said pipettes; and
(m) repeating steps b through k until a desired number of transfers or dilutions are completed.

14. The method of claim 13 wherein step i includes at least once after expelling liquid into said other receptacles, withdrawing liquid from said other receptacles into said pipettes to effect mixing of the contents of the other receptacles with the added liquid.

15. The method of claim 13 wherein expelling of liquids in said pipettes in step i includes actuation of a plunger in each pipette while said tips are just above the meniscus of liquid in said receptacles to expel any remaining liquid in said tips through capillary attraction between liquid in said tips and said receptacles.

16. The method of claim 13 further including the step of detecting whether all of the tips in a row are successfully picked up during step d.

17. The method of claim 13 wherein said tips are discharged onto said second work station during step k.

18. The method of claim 13 which includes the further step of detecting whether all tips having been ejected after step l.

19. The method of claim 13 wherein said steps c through j are repeated before steps k through m are performed.

20. An apparatus for handling small liquid samples during filling, transferring or mixing of such liquid samples by repetitive use of the same pipette to transfer liquids between a plurality of sample receptacles having different quantities or types of liquid therein which includes a plurality of syringes, each having a barrel portion and a pipette tip member securable thereto for insertion into said sample receptacles to withdraw liquids from or inject liquids into said receptacles, and each syringe barrel including a body portion having a cylinder formed therein, a plunger positioned in and fluid sealed for reciprocal motion of said plunger through said cylinder;
an elongated pipette tip member for covering the other end of said cylinder and forming a substantial portion of the fluid volume of said barrel, said tip member having one end frictionally engageable with a portion of the sidewall surface of said body portion to form a fluid seal with said cylinder;
reciprocal means having a member slidably surrounding the exterior of said barrel to contact said tip member to frictionally disengage said tip member from said sidewall surface,
means for supporting a plurality of said pipette tip members in a vertical position for selective frictional engagement with said sidewall surface,
means for reciprocating each of said barrels to frictionally engage said tips with said surface, and
means for actuating said reciprocal means to disengage said tip member from said cylinder, whereby a different pipette tip member may be selectively and automatically changed after any insertion into fluid in a sample receptacle.

21. Apparatus in accordance with claim 20 wherein each of said syringe barrels is resiliently mounted to permit compliance between said barrel portion and said pipette tip member to permit pick up of said tip members of slightly different dimensions.

22. A method for effecting automatic transfer or dilution of liquid samples between a plurality of liquid receptacles comprising the steps of:
(a) positioning said plurality of liquid receptacles for horizontal movement on a support table with said receptacles being indexable beneath a row of pipettes at a first work station, at least one of said liquid receptacles containing a predetermined volume of liquid;
(b) positioning a row of pipettes on a head assembly above said support table and vertically reciprocable relative thereto;
(c) arranging at least a row of pipette tips for horizontal movement on said support table at a second work station thereon;
(d) moving said support table to register said row of pipette tips with the pipettes on said head assembly;
(e) lowering said pipettes to engage the tips in the registered row and picking up the engaged tips;
(f) moving said table to index said liquid-containing receptacles at said first work station under said row of pipettes;

(g) inserting the engaged tips in the liquid in said liquid-containing receptacles and withdrawing at least some of the liquid therefrom into said pipettes;
(h) raising said pipettes;
(i) moving said table to index one or more other receptacles under said pipettes;
(j) lowering said pipettes and expelling the liquid in said pipettes into the other receptacles;
(k) raising said pipettes;
(l) moving the table to bring a selected position at said second work station into alignment with said pipettes; and
(m) discharging said engaged tips from said pipettes.

23. The method of claim 22 which includes repeating steps c through l for successive rows of tips and successive receptacles at said respective work stations until a desired number of transfers or dilutions are completed.

24. The method of claim 22 wherein step j includes at least once after expelling liquid into said receptacle, withdrawing liquid from said receptacle into said pipettes and again expelling liquid from said pipettes to effect mixing of the contents of said receptacles with the added liquid.

25. The method of claim 22 wherein expelling of liquids in said pipettes in step j includes actuation of a plunger in each pipette while said tips are just above the meniscus of liquid in said receptacles to expel any remaining liquid in said tips through capillary attraction between liquid in said tips and said receptacle.

* * * * *